(12) United States Patent
Heneveld

(10) Patent No.: US 10,299,774 B2
(45) Date of Patent: May 28, 2019

(54) DUAL INSUFFLATION AND WOUND CLOSURE METHODS

(71) Applicant: SUTURE EASE, INC., San Jose, CA (US)

(72) Inventor: Scott Heneveld, Whitmore, CA (US)

(73) Assignee: SUTURE EASE, INC., San Jose, CA (US)

( * ) Notice: Subject to any disclaimer, the term of this patent is extended or adjusted under 35 U.S.C. 154(b) by 296 days.

(21) Appl. No.: 14/825,452

(22) Filed: Aug. 13, 2015

(65) Prior Publication Data

US 2015/0342582 A1 Dec. 3, 2015

Related U.S. Application Data

(63) Continuation of application No. 13/365,818, filed on Feb. 3, 2012, now abandoned.

(60) Provisional application No. 61/574,455, filed on Aug. 4, 2011.

(51) Int. Cl.
| | | |
|---|---|---|
| A61B 17/04 | (2006.01) | |
| A61B 17/34 | (2006.01) | |
| A61B 17/00 | (2006.01) | |
| A61B 17/29 | (2006.01) | |

(52) U.S. Cl.
CPC ...... *A61B 17/0057* (2013.01); *A61B 17/0482* (2013.01); *A61B 17/0485* (2013.01); *A61B 2017/00637* (2013.01); *A61B 2017/00663* (2013.01); *A61B 2017/00867* (2013.01); *A61B 2017/2911* (2013.01); *A61B 2017/3484* (2013.01)

(58) Field of Classification Search
CPC ............ A61B 17/0482; A61B 17/0469; A61B 17/0485; A61B 17/0057; A61B 2017/00637; A61B 2017/00663; A61B 2017/0472; A61B 2017/3484; A61B 2017/3482; A61B 2017/348; A61M 25/02; A61M 25/04; A61M 2025/0233
See application file for complete search history.

(56) References Cited

U.S. PATENT DOCUMENTS

| | | | | |
|---|---|---|---|---|
| 3,903,892 | A * | 9/1975 | Komiya | A61B 1/00098 |
| | | | | 606/110 |
| 4,043,338 | A * | 8/1977 | Homm | A61M 31/00 |
| | | | | 604/105 |
| 5,122,122 | A | 6/1992 | Allgood | |
| 5,290,249 | A * | 3/1994 | Foster | A61B 17/34 |
| | | | | 604/174 |
| 5,391,182 | A | 2/1995 | Chin | |

(Continued)

*Primary Examiner* — Christopher L Templeton
(74) *Attorney, Agent, or Firm* — Innovation Capital Law Group, LLP; Vic Lin

(57) ABSTRACT

A dual functioning instrument set, comprising a needle and guide, has not only the capabilities to enter and insufflate the abdominal cavity but also the ability of a suture passer to carry and retrieve suture for closure of the incision sites at the end of the procedure. The needle contains a deployable snare that is used to pass and retrieve suture. The guide is used to repeatedly locate the needle relative to the inner abdominal wall allowing for consistent placement of sutures. For insufflation purposes, obturator tips having different distal structures are provided for shielding the sharp needle tip after insertion through a body wall.

12 Claims, 15 Drawing Sheets

(56) References Cited

U.S. PATENT DOCUMENTS

| | | | |
|---|---|---|---|
| 5,501,692 A * | 3/1996 | Riza | A61B 17/0469 112/169 |
| 5,507,758 A * | 4/1996 | Thomason | A61B 17/0469 606/139 |
| 5,562,686 A | 10/1996 | Sauer et al. | |
| 5,562,688 A * | 10/1996 | Riza | A61B 17/0469 606/139 |
| 5,591,180 A | 1/1997 | Hinchliffe | |
| 5,716,369 A * | 2/1998 | Riza | A61B 17/0469 606/139 |
| 5,749,826 A * | 5/1998 | Faulkner | A61F 2/0009 128/DIG. 25 |
| 5,827,299 A * | 10/1998 | Thomason | A61B 17/0469 606/139 |
| 5,954,734 A * | 9/1999 | Thomason | A61B 17/0469 606/139 |
| 6,066,146 A | 5/2000 | Carroll et al. | |
| 6,743,241 B2 | 6/2004 | Kerr | |
| 7,824,419 B2 | 11/2010 | Boraiah | |
| 2004/0068273 A1 | 4/2004 | Fariss et al. | |
| 2004/0225301 A1* | 11/2004 | Roop | A61B 17/0057 606/148 |
| 2005/0021055 A1* | 1/2005 | Toubia | A61B 17/0057 606/144 |
| 2005/0121042 A1* | 6/2005 | Belhe | A61B 17/0057 128/887 |
| 2005/0187578 A1* | 8/2005 | Rosenberg | A61M 25/04 606/232 |
| 2006/0030868 A1 | 2/2006 | Bennett | |
| 2006/0100544 A1* | 5/2006 | Ayala | A61M 25/0136 600/585 |
| 2006/0167475 A1 | 7/2006 | Bischof et al. | |
| 2006/0264978 A1* | 11/2006 | Belhe | A61B 17/0057 606/150 |
| 2007/0203507 A1 | 8/2007 | McLaughlin et al. | |
| 2008/0033459 A1 | 2/2008 | Shafi et al. | |
| 2008/0097485 A1* | 4/2008 | Shpaichler | A61B 17/3421 606/148 |
| 2010/0185155 A1* | 7/2010 | McMichael | A61J 15/0065 604/175 |
| 2010/0324573 A1 | 12/2010 | Toubia et al. | |
| 2011/0082475 A1* | 4/2011 | Smith | A61B 17/0057 606/144 |
| 2011/0112557 A1* | 5/2011 | Beeley | A61B 17/0057 606/148 |
| 2012/0016385 A1 | 1/2012 | Keren et al. | |
| 2012/0035623 A1 | 2/2012 | Bagaoisan et al. | |
| 2013/0165956 A1* | 6/2013 | Sherts | A61B 17/0482 606/148 |

\* cited by examiner

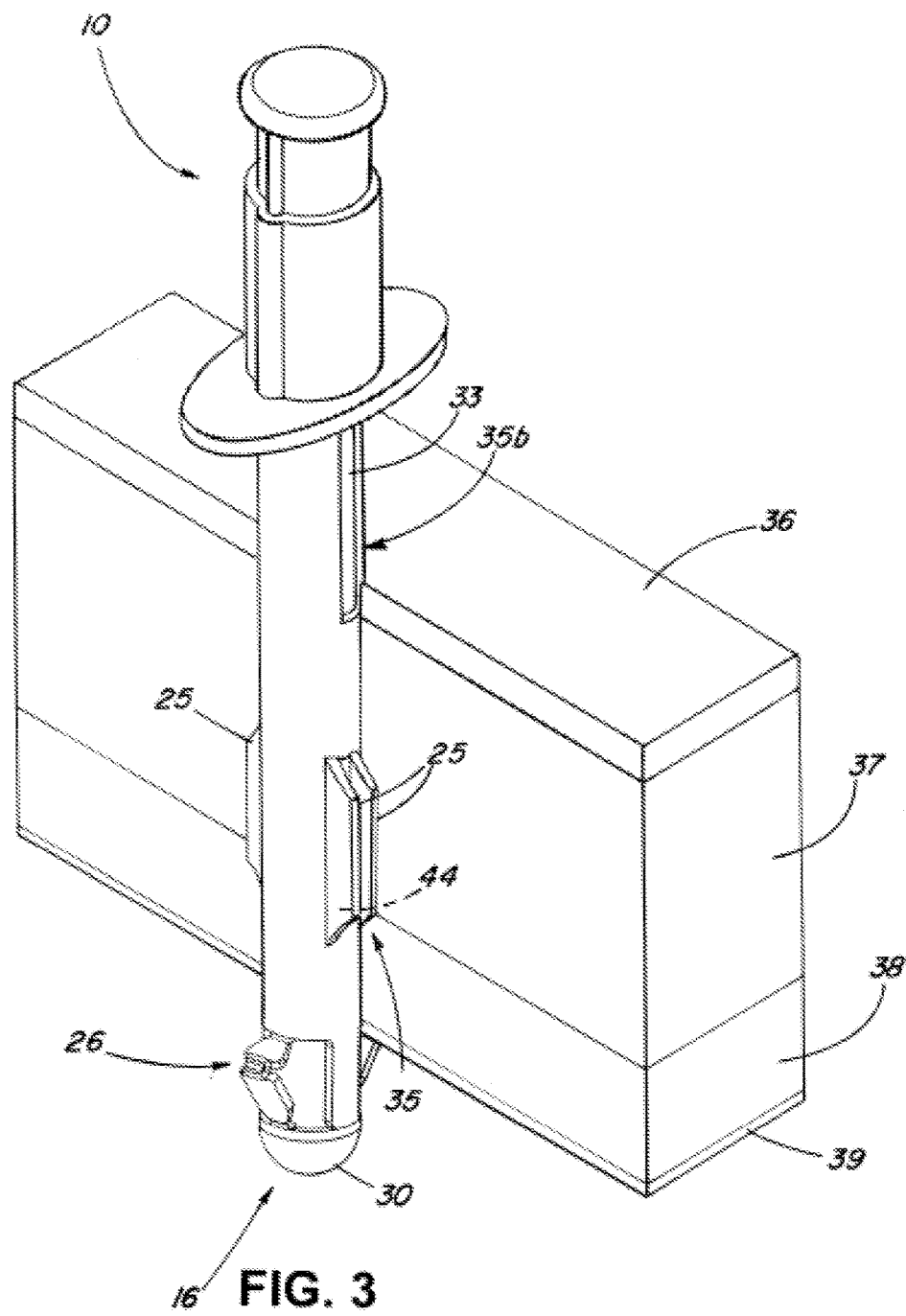

FIG. 8A
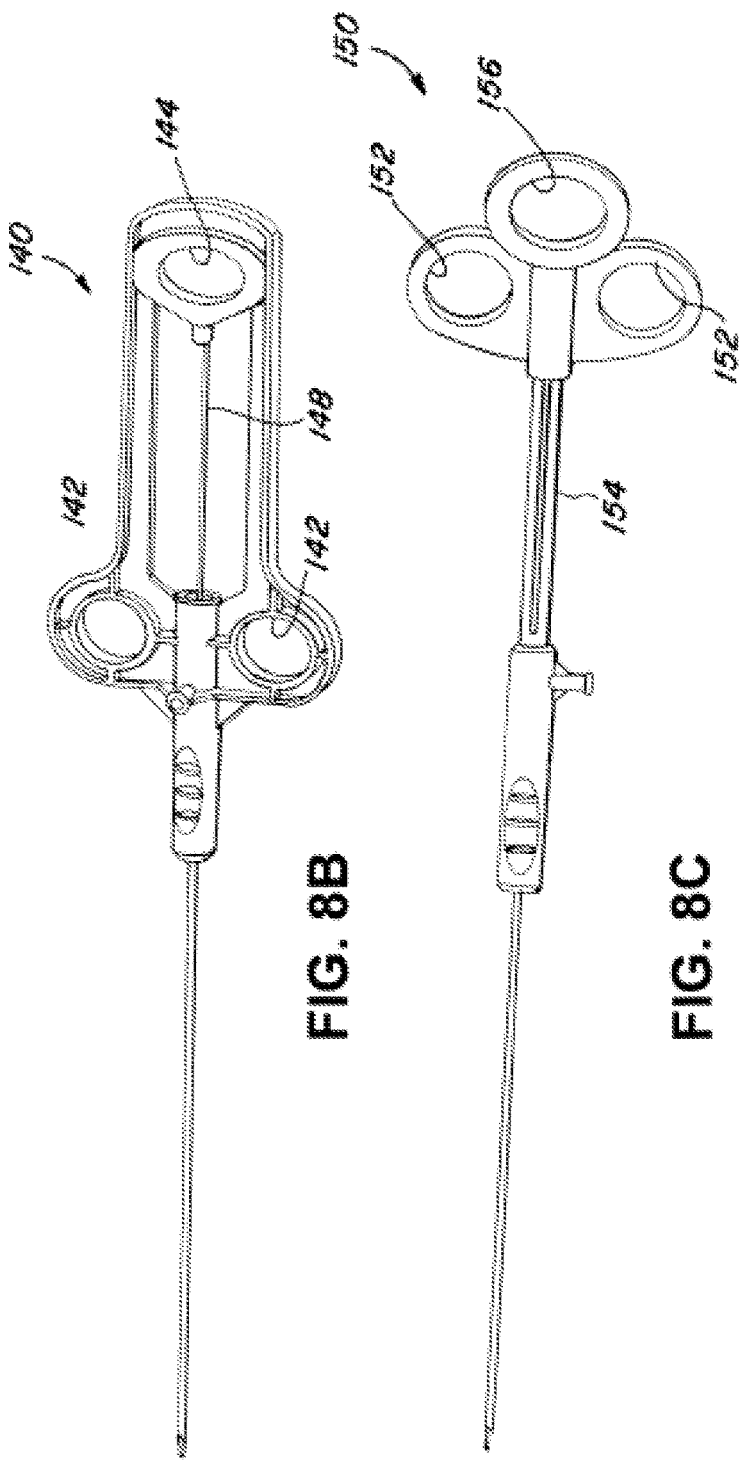
FIG. 8B
FIG. 8C

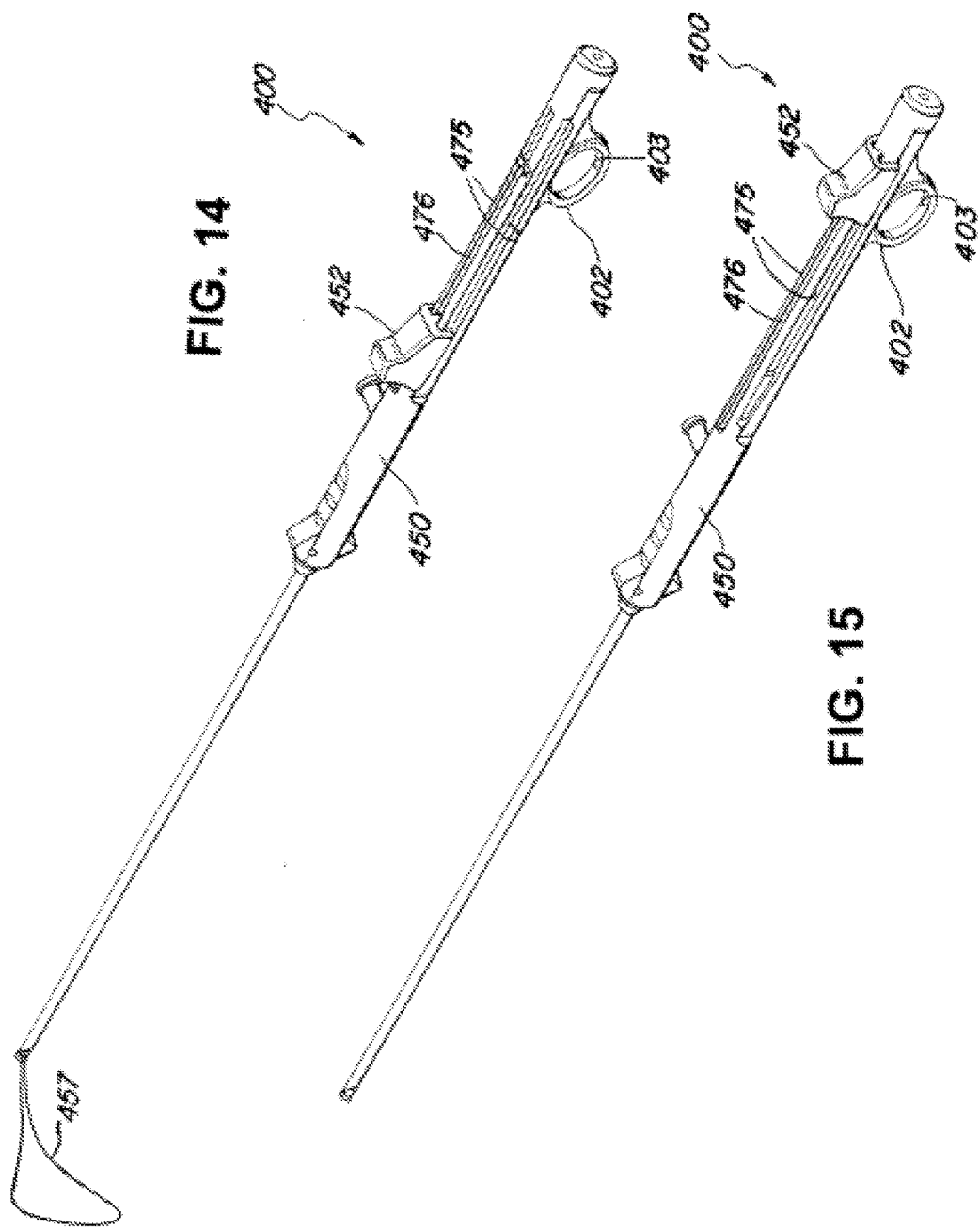

DUAL INSUFFLATION AND WOUND CLOSURE METHODS

RELATED APPLICATIONS

This application is a continuation of U.S. Non-Provisional patent application Ser. No. 13/365,818 filed on Feb. 3, 2012, now abandoned, which is the Non-Provisional of U.S. Provisional Patent Application Ser. No. 61/574,455 filed on Aug. 4, 2011 and entitled "INSUFFLATION/CLOSURE DEVICE AND GUIDE.", the disclosure of which is incorporated by reference herein.

BACKGROUND OF THE INVENTION

1. Field of the Invention

This invention relates to surgical instruments for approximation, ligation and fixation of tissue using a suture, and particularly to the approximation of tissue separated by means of an endosurgical trocar being inserted into a body cavity. This invention also relates to the access to an anatomic cavity or space during a medical procedure, and particularly to insufflations of the abdominal cavity for laparoscopic surgery.

2. Description of Prior Art and Related Information

Numerous methods currently exist for performing laparoscopic procedures. One of the more commonly used methods is known as closed laparoscopy which utilizes a sharp needle (eg. Veress needle) to puncture the abdominal wall and insufflate the abdominal cavity with an inert gas such as carbon dioxide through the needle. This process of insufflating the cavity separates the abdominal wall from the underlying organs creating a gap for the surgeon to work within. A trocar/cannula system is then used to maintain the insufflated cavity and provide a working portal for which instruments can be passed into and out of the abdominal cavity to perform various surgical procedures. When the procedure is completed, it is desirable for the surgeon to close the incision site using suture material to minimize the risk of adverse post-operative events.

Insertion of the needle into the abdomen is performed without any visual aid to facilitate location of the sharp needlepoint. In order to reduce the probability of inadvertent penetration of delicate internal organs in this "blind" procedure, the sharp insufflation needle contains a rounded member disposed within the lumen of the needle, and biased by a spring to an extended position beyond the needle tip.

The conventional insufflation needle also includes a means for introducing an inert gas into the abdominal cavity through a channel or opening within the lumen of the needle. A luer or other quick connect type adapter is typically housed within the proximal handle of the needle to connect a gas source to the needle. The gas then travels from the handle through the length of the needle and exits into the body cavity from the distal tip of the needle.

One of the post-operative complications associated with this procedure is the incidence of trocar site hernias, where a portion of an organ or fatty tissue protrudes out through the hole in the abdominal wall created by the trocar access portal. It is believed that improper closure, or complete lack of closure, of the incision site at the peritoneum is the primary cause of these hernias which form during the post-operative period ranging from several days to several months following the procedure. Traditional methods of wound site close require an additional set of instruments (suture passers, guides, etc.) to be introduced into the surgery. A number of these instruments have been previously disclosed. However, the prior art related to trocar wound site closure instrumentation are typically cumbersome to use and do not provide for a simple, reproducible, and reliable means of closing the wound site.

In order to safely perform a closed laparoscopic procedure, both a Veress needle and a suture passing device may be purchased and used for the completion of the procedure. This can be both expensive and create additional waste, unnecessarily. The present invention comprises a combination device that can provides the multiple functions that were not previously offered in the prior art.

BRIEF SUMMARY OF THE INVENTION

In accordance with the present invention, structures and associated methods are disclosed which address these needs and overcome the deficiencies of the prior art. A preferred system according to the invention comprises a surgical instrument as well as a surgical instrument set that may have one or two basic functions.

First, the system may have the capabilities to provide entry into the abdominal cavity and subsequently insufflating the cavity for use in laparoscopic surgical procedures. In the preferred embodiment, the system comprises a needle apparatus having a sharp needle tip and an insufflation channel to facilitate penetration into the abdominal cavity and insufflation. A unique obturator tip is provided to shield the sharp needle tip upon insertion into the cavity.

Second, the system may have the capabilities to close the fascial/peritoneal layer at the trocar wound site in a quick, consistent and reproducible manner at the end of the procedure. To facilitate closure of the wound, the system includes a guide used in combination with the same needle apparatus which also serves as a suture engaging device. In the preferred embodiment, the system would have both of the capabilities described above.

The needle apparatus may be able to function like a suture passer, in that it has the ability to carry and retrieve suture through tissue layers for suturing closed the wound site. The needle also has the ability to insufflate the abdomen during the laparoscopic procedure. The needle apparatus may comprise several components including: a handle, actuation mechanisms, means for connecting the needle to a gas line, a deployable snare, a needle tip, a hollow inner shaft inside the needle tip, and a safety mechanism plunger disposed within the needle tip.

In a preferred embodiment, a handle at the proximal end of the needle apparatus allows for single-handed or double-handed use. An actuator mechanism is disposed adjacent to the handle and configured for the deployment and retraction of the snare used to pass and retrieve the suture material. The preferred actuator mechanism may include a first actuator comprising sliding trigger that translates along the long axis of the handle that locks the snare against the needle when it is in one position, and partially deploys the snare loop when the trigger is set into a second position. This trigger may be spring loaded to ease the deployment of the snare from within the needle. A second actuator may comprise a sliding plunger, or extender rod, that exits from the proximal end of the handle and translates along the long axis of the handle. This extender rod would be used to fully deploy the snare. The handle and actuator means may be constructed from metals (such as stainless steel, titanium, or aluminum) or plastics (such as polyacetal, nylon, PEEK, or polycarbontae), or any combination of the two.

The snare accomplishes the suture passing capabilities of the needle apparatus. As previously stated, the snare may be actuated between three different positions: (1) completely retracted into the needle shaft, (2) partially deployed, and (3) fully deployed. When the snare is completely retracted into the needle shaft, the suture material would be captured between the snare and the inner shaft of the needle apparatus. When the snare is partially deployed, a small loop section of the snare would be exposed. This partial deployment of the snare may allow for certain simple suture passing steps to be accomplished without having to fully deploy the snare. When the snare is fully deployed, a larger loop section of the snare would be exposed that is significantly greater in size than the partially deployed loop. The fully deployed snare would be most useful when trying to retrieve the free end of the suture within the body cavity by providing a large target in which the suture can be grasped. Optimally, the snare would be deployed perpendicular to the long axis of the needle to simplify the suture passing process, however the snare may be deployed over a broader range of angles from the needle ranging from 0-180 degrees relative to the long axis of the needle. The snare would most optimally be manufactured from a shape memory alloy material such as Nitinol, but may also be made from other metallic or polymeric wire materials.

A long outer needle shaft may be connected to the proximal handle and extends distally over a length that may range from 1-15 inches. The outer needle shaft may have a sharp tip, or needle peak, at the distal-most point to ease the insertion of the needle through the various tissue layers. The outer shaft may house an inner shaft that has a hollow, unobstructed inner lumen. This unobstructed inner lumen may allow for the passage of an inert gas for insufflation of the abdomen. A luer connector or other quick connect type device may be disposed on the proximal handle to provide an entry passageway for the gas to enter into the needle. The unobstructed inner lumen may also provide a passageway for the snare material to travel up through the needle portion and into the handle so that it can be connected to the actuator mechanism.

The distal-most end of the inner shaft may have a blunt obturator attached to the tip. The entire inner shaft may be spring loaded to allow for the blunt obturator to translate away from the tip of the needle when it is loaded, and passively travel back to the tip of the needle when it is unloaded. The obturator spring may be housed within the handle. The spring loaded obturator would serve as a safety mechanism for protecting the internal organs within the abdomen. The inner and outer needle shafts would optimally be constructed from metallic tubes such as stainless steel. The obturator tip may be manufactured from a number of different materials including, but not limited to, metals and plastics.

In another preferred embodiment, the needle apparatus may have a single actuator to control the snare between a fully exposed position and a fully retracted position. The single actuator may comprise a lockout trigger similar to the first preferred embodiment, except that the lockout trigger can proximally translate with respect to the housing a greater distance so as to proximally push the slide rod connected to snare all the way to fully expose the snare.

The guide apparatus may be used to guide the needle through the abdominal wall in a repeatable manner. The guide may comprise an outer housing, or barrel, and an inner plunger used to actuate the guide.

The barrel may have two or more counterforce tabs, or extension tabs, at the proximal end to aid in the handling and insertion of the guide into the abdomen. These counterforce tabs may provide surfaces for the user to utilize two fingers to hold the barrel. For example, the index finger would be placed under one tab, and the middle finger is placed under the second tab. The thumb may then be used to actuate the proximal surface of the plunger and secure the guide within the user's grasp.

The distal end of the barrel would have a blunt tip to minimize the potential of harm or damage to the adjacent tissue during insertion. Just proximal to the blunt tip the barrel may have a deformable securing mechanism that may have two configurations. The first configuration of the deformable section would be aligned with the wall of the outer housing such that the structure has a slender, continuous outer diameter. This first slender position would be utilized during the insertion of the guide into the cavity. The deformable section can then be deformed to a second flared out position where securing mechanism extends beyond the outer diameter of the outer housing. The securing mechanism, comprising expanding feet in the preferred embodiment, is used to place the guide against the inner wall of the abdomen to provide a reference point for the needle to be repeatedly placed in the same location of the abdominal wall that is required to be sutured for closure of the portal site.

Along the central portion of the shaft of the barrel are multiple slots in the shaft wall. These slots serve to provide a passageway for the needle apparatus to travel to the appropriate location of the abdominal wall for the placement of sutures. Two slots may be placed opposing each other near the proximal end of the shaft, and two additional slots may be placed opposing each other near the distal end of the shaft. The proximal slots may serve as the entry points for the needle, while the distal slots may serve as the exit points for the needle. The guide also includes axial wings, which may be extruded, extending away from the central axis of the shaft to aid in pushing away fatty tissue that is undesirable tissue for the suture to pass through. Particularly if these features are located near the distal slots where the needle is exiting the guide, the risk of suturing unwanted fatty tissue is minimized.

The guide may comprise a plunger slidably disposed within the barrel. The plunger may be used to actuate the expanding feet, comprising living hinges in the preferred embodiment, on the barrel. This plunger may be spring loaded such that the plunger is biased to the radially expanded position. When the plunger is in the biased flared out position, the feet would be in the expanded position. When the plunger is pressed to the first position, the feet would be retracted back to a position that aligns the outer diameter of the outer housing in a continuous slender fashion. The plunger may be attached to the distal end of the barrel. Along the shaft of the plunger would be through holes that align with the outer housing slots to accommodate passage of the needle apparatus through the guide. These through holes may intersect each other, or may be offset such that the holes do not intersect one another. All of the guide components would preferably be made from an injection moldable polymer (such as polycarbonate, polyacetal, nylon, or ABS) but the guide may be machined from other plastics and/or metals.

The basic procedural steps for abdominal entry and insufflation of the cavity may flow as follows. The needle is used to enter the abdominal cavity using standard closed laparoscopic techniques. A gas line is connected to the handle allow for an inert gas to be passed into the abdominal cavity. The inert gas is then turned on until the cavity reaches an appropriate level of insufflation to allow for the procedure to be performed with appropriate visualization. The needle is then removed, and a trocar is inserted into the puncture site to perform the procedure.

The basic procedural steps of the utilization of the suturing system may flow as follows. At the end of the surgical procedure, the trocar is removed and the needle guide is placed into the wound. The expandable feet are deployed against the inner wall of the peritoneum. A short end of a suture tail is captured within the snare, while outside the body cavity. Then the needle apparatus is advanced through the needle guide and tissue layers into the abdominal cavity, carrying the suture with it. The snare is expanded to release the suture. The needle apparatus is then removed from the guide and reinserted through the opposite side of the guide on the opposite side of the puncture wound. When the distal end of the assembly is exposed in the abdominal cavity, the snare is expanded to provide an easy target to secure the existing suture tail inside the abdominal cavity. Once the suture has been secured within the wire snare, the needle apparatus is removed to outside the body cavity, bringing the suture along with it. The suture is then released from the snare wire. The suture is in place to be tied with a knot to provide closure the trocar puncture site. This suturing procedure may also be accomplished without the use of the needle guide.

BRIEF DESCRIPTION OF THE DRAWINGS

FIG. 3 shows the guide as it is placed through a section of tissue with the expanded feet resting against the inner peritoneal wall;

FIGS. 8A-C show various alternative embodiments of the handle portion of the needle;

FIG. 14 is a perspective view of a second preferred embodiment of a needle apparatus comprising a single actuator mechanism with the snare in the fully exposed position;

FIG. 15 is a perspective view of the second preferred needle apparatus showing the snare in the fully retracted position.

The various embodiments of the invention can now be better understood by turning to the following detailed description wherein illustrated embodiments are described. It is to be expressly understood that the illustrated embodiments are set forth as examples and not by way of limitations on the invention as ultimately defined in the claims.

DETAILED DESCRIPTION OF THE PREFERRED EMBODIMENTS AND BEST MODE OF INVENTION

In a preferred embodiment, a system 100 is provided for insufflating an abdominal cavity and closing a trocar wound site. The system 100 comprises a guide and a single device having dual functionalities of insufflation and suture engagement.

FIGS. 1A-1D illustrate a preferred embodiment of a surgical guide apparatus, or simply guide, 10 for directing surgical instruments through a body wall. The guide 10 may be particularly useful for directing suturing devices used in closing wounds, or openings through body walls, made in surgical procedures to access internal body cavities. The guide 10 comprises a radially expandable securing mechanism 26 at a distal end 16 that is configured to secure the guide 10 to the inner wall of a body cavity, such as the peritoneum surrounding an abdominal cavity in the case of a laparoscopic procedure.

Figure 1A:
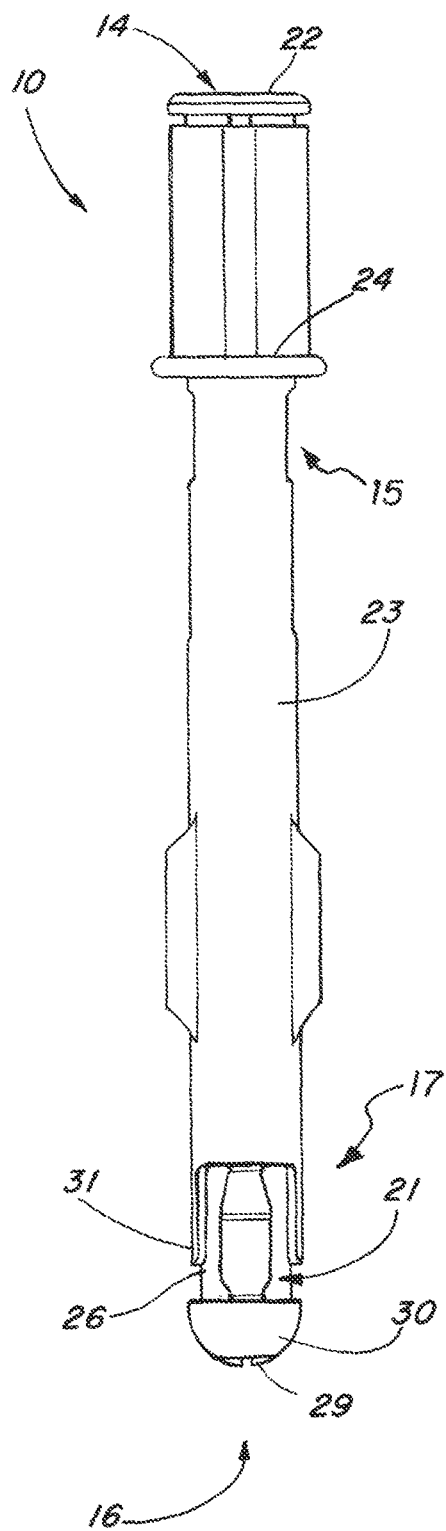
FIGS. 1A-1B show a preferred embodiment of a needle guide in an actuated position with a securing mechanism not expanded.

In FIG. 1A, a plunger 21 is slidably disposed within a barrel 23 having a barrel proximal portion 15 and a barrel distal portion 17. The plunger 21 and barrel 23 may be connected to each other by deformable locking tabs 29 at a distal end 12 of the plunger 21, that lock within the blunt distal end cap 30 of the barrel 23. At a proximal end 14 of the plunger 21 is an actuation surface 22 that may be flat or contoured that allows for the plunger to be pressed down to slide the plunger 21 within the barrel 23.

Figure 1B:
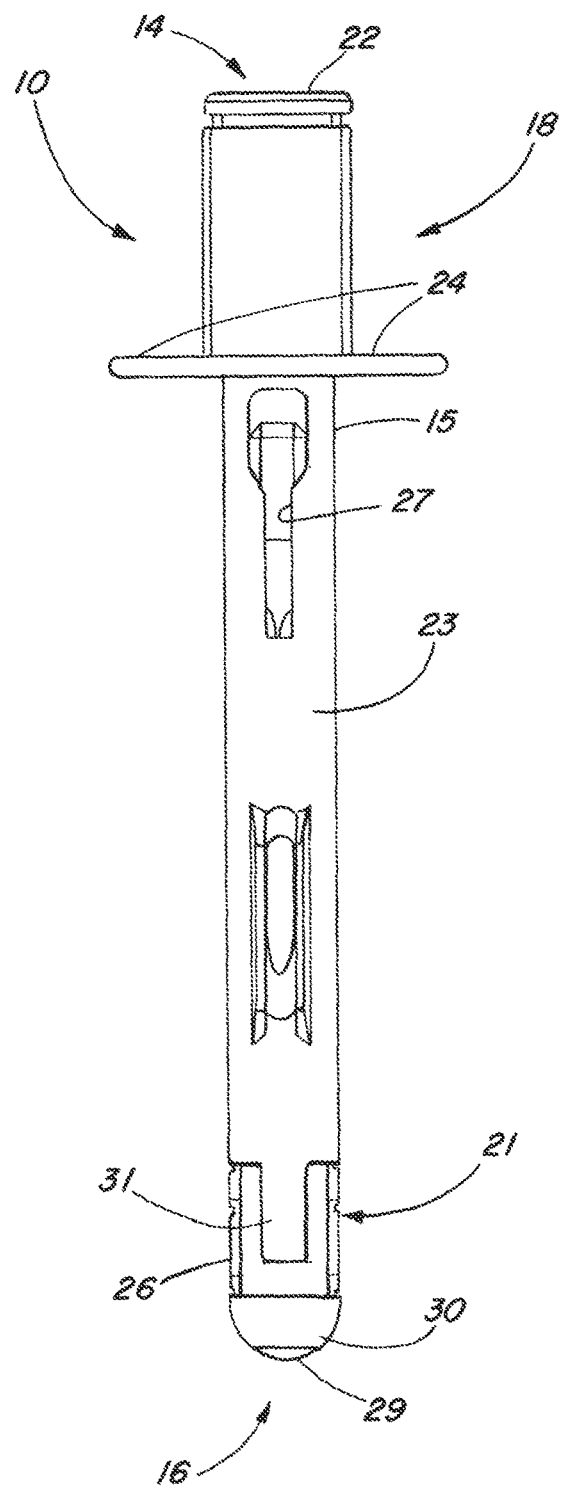
Figure 1C:
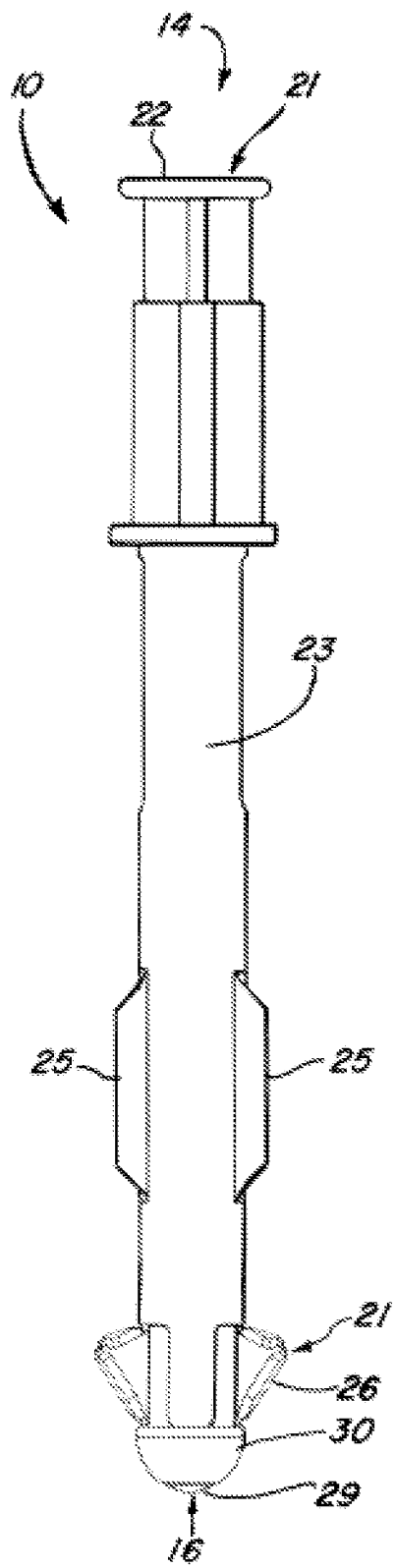
FIGS. 1C-1D show the preferred needle guide in the resting position with the securing mechanism expanded.
Figure 1D:
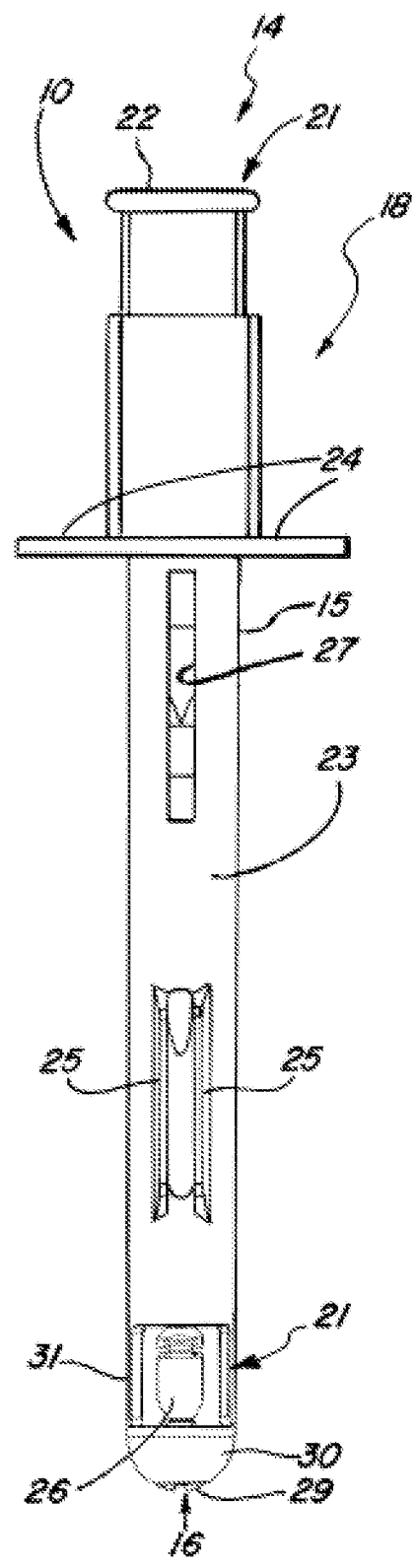

As the plunger 21 translates with respect to the barrel 23, the radially expandable securing mechanism 26 at the distal end 16 of the barrel 23 moves between two positions of radially expanded, or flared out, as shown in FIGS. 1C and 1D, and radially contracted, or slender, as seen in FIGS. 1A and 1B. In the preferred embodiment, the internal cavity securing mechanism 26 comprises two or more expanding feet 26 radially spaced apart from each other. The expanding feet 26 each preferably comprise a living hinge section composed of the same material as the barrel 23, where the material is cut thin at specific locations allowing for the material to flex. It is to be expressly understood that the radially expandable securing mechanism 26 may comprise a variety of structures capable of moving between slender and flared-out configurations. Radially adjacent to the expanding feet 26 may be one or more distally extending stop tabs 31 on the barrel, as shown in FIGS. 1A and 1B. The stop tabs 31 are configured to provide a mechanical stop for the distal end cap 30 of the barrel 23 to collide against to prevent the plunger 21 from over-translating and potentially damaging the thin section of material within the expanding feet 26.

In FIGS. 1B and 1D, wwo counterforce tabs, or extension tabs, 24 are preferably disposed near a proximal end 18 of the barrel 23 and configured to be grasped with one or more fingers while the thumb may be used to press down on the actuation surface 22. The counterforce tabs 24 facilitate ease of handling of the guide 10. The guide 10 comprises at least one needle entry slot 27 in the barrel proximal portion 15 preferably distal to the counterforce tabs 24.

Figure 2:
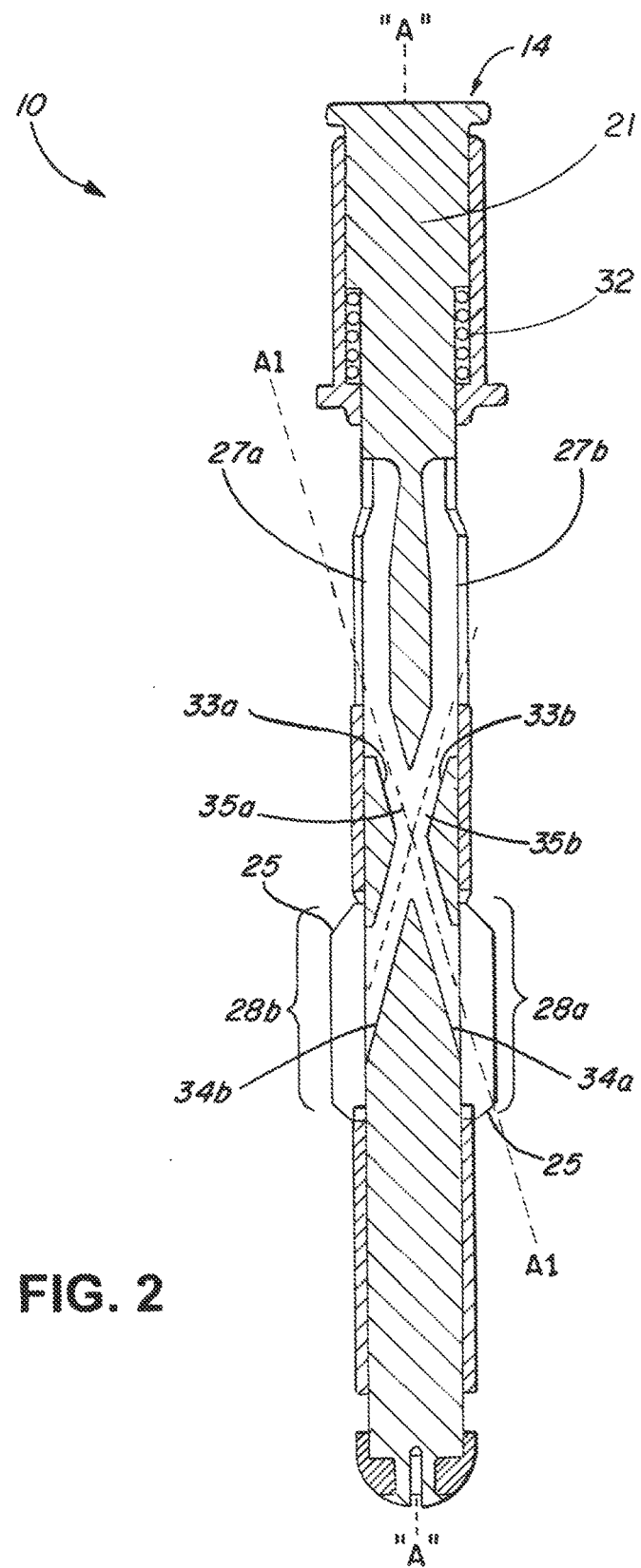
FIG. 2 is a cross sectional view of the preferred needle guide showing the needle tracks.

In the preferred embodiment, the guide 10 provides two different, diagonal pathways for a needle apparatus and thus comprises first and second entry slots 27a, 27b as more clearly shown in FIG. 2. These barrel entry slots 27a, 27b provide for entry points for a suture engaging device, or needle apparatus, to enter the guide 10. The two barrel entry slots 27a, 27b are preferably axial in that they 27a, 27b extend over a length that is parallel to a long axis "A" of the guide 10. The barrel entry slots 27a, 27b are preferably equally spaced apart in a radial manner from each other, i.e., 180 degrees apart if there are two slots, 120 degrees apart if there are three slots, etc. The guide 10 comprises barrel exit slots 28a, 28b equal in number to the entry slots 27a, 27b and located distally along the barrel 23.

The guide 10 is useful for directing suture engaging devices, and particularly a preferred embodiment of a suture engaging device discussed further below and identified simply as a needle apparatus. Accordingly, the guide 10 preferably comprises two pathways diagonal to each other and oriented to direct a needle apparatus to both a first internal location to carry and release a suture, and a second internal location preferably horizontally opposite to the first internal location in order to facilitate retrieval of the suture using the preferred suture engaging device discussed further below.

FIG. 2 is a cross sectional view of the guide 10 showing the preferred dual pathways that a surgical instrument, such as a needle apparatus or suture engaging device, can take through the guide 10. The guide 10 preferably comprises first and second plunger entry points 33a, 33b adjacent to the plunger proximal end 14 and first and second plunger exit points 34a, 34b adjacent to the plunger distal end 16. A first tunnel, or first track, 35a defines a first track axis "A1" and is in communication with both the first plunger entry 33a formed on a first side of the plunger 21 and the first plunger exit 34a which is preferably formed on an opposing side of the plunger 21. The first entry 33a, first tunnel 35a and first exit 34a collectively form a first needle pathway that is preferably oblique to the guide axis "A."

A second tunnel, or second track, 35b is in communication with both the second plunger entry 33b formed on the second side of the plunger 21 and the second plunger exit 34n which is preferably formed on the opposing first side of the plunger 21. Thus, the first and second tunnels 35a, 35b are preferably off-axis and diagonal to each other. These tunnels 35a, 35b may intersect each other as shown, or have their paths offset such that they do no intersect. The second entry 33b, second tunnel 35b and second exit 34b collec-tively form a second needle pathway oblique to the guide axis "A" and diagonal to the first pathway. The plunger 21 on the guide 10 may be passively controlled by a spring 32 that is housed between the plunger 21 and barrel 23 to keep the guide in the biased open position with the feet 26 expanded. It will be appreciated that biasing the guide 10 to this hands-free operative configuration with the feet 26 expanded and the pathways open frees up both of the surgeon's hands to work with other instruments when the guide 10 is inserted into the trocar wound.

The barrel needle exit slots 28 may be surrounded by up to two opposing tissue distraction wings 25. These wings 25 help separate unwanted tissue away from the needle exit slots 28.

In the case of a laparoscopic surgery involving use of a trocar, the guide 10 may be placed through the tissue layers of the open trocar wound site as shown in FIG. 3 after the trocar has been removed. This tissue may consist of the skin 36, adipose tissue 37, muscle and fascia 38 and peritoneal layer 39. Prior to insertion of the guide 10, the feet 26 are in the slender, non-expanded position with the plunger 21 pressed. Once the distal end 12 of the guide 10 is appropriately placed under the peritoneal layer, the plunger 21 is released and spring-biased to the operative configuration causing the living hinges 26 to expand as shown in FIG. 3. With the radially expandable securing mechanism 26 in the flared out configuration, the guide 10 can then be pulled up against the inner peritoneum to align the needle tunnels 35a, 35b with the appropriate tissue layers for suturing. The plunger entry holes 33 for the needle apparatus are positioned above the outer skin layer 36, while the plunger exit holes 34 for the needle apparatus should be positioned just above the muscle and fascia layer 38 to be sutured. The tissue distraction wings 25 aid in pushing away unwanted adipose 37 or fatty tissue from the needle exit holes 34 such that primarily muscle and fascia tissue 38 is sutured.

Figure 4A:
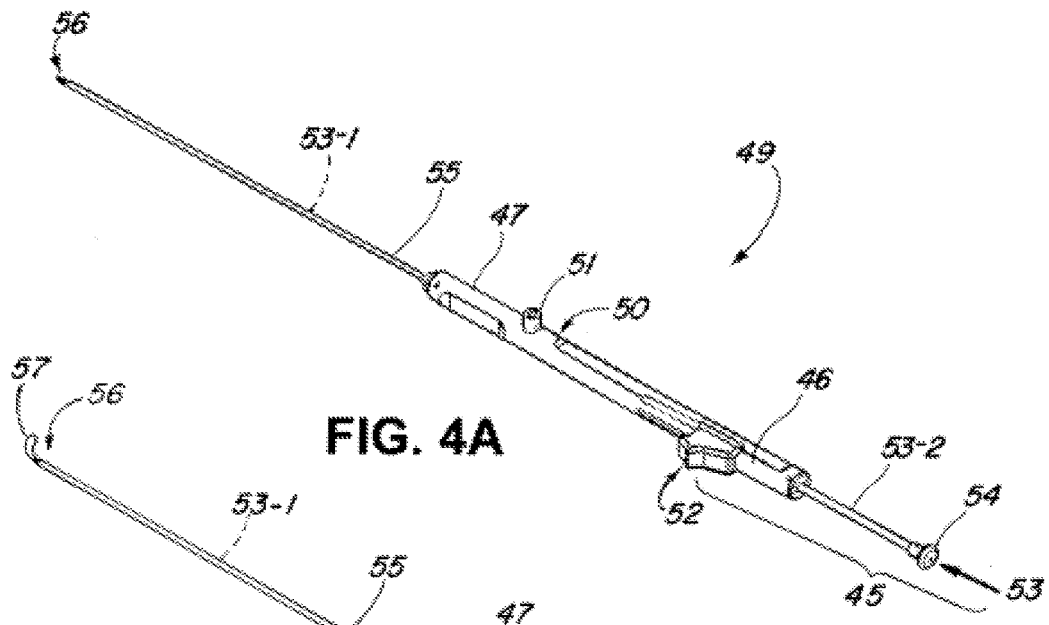
FIG. 4A shows an oblique view of the needle with the snare fully retracted into the needle.
Figure 4B:
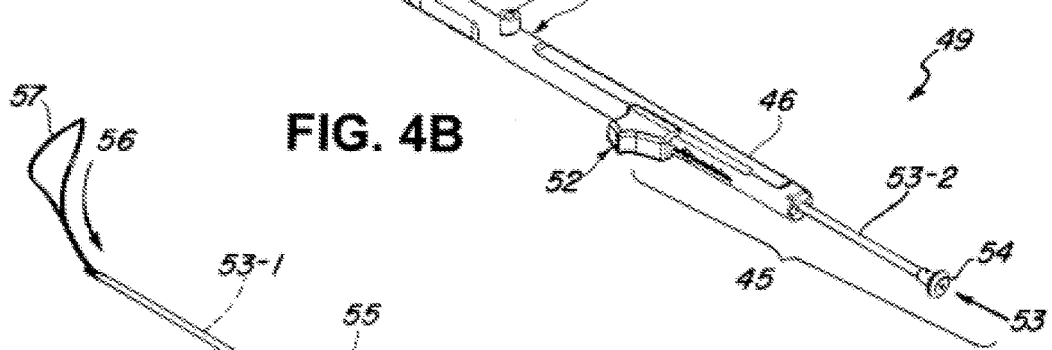
FIG. 4B shows an oblique view of the needle with the snare partially extended.
Figure 4C:
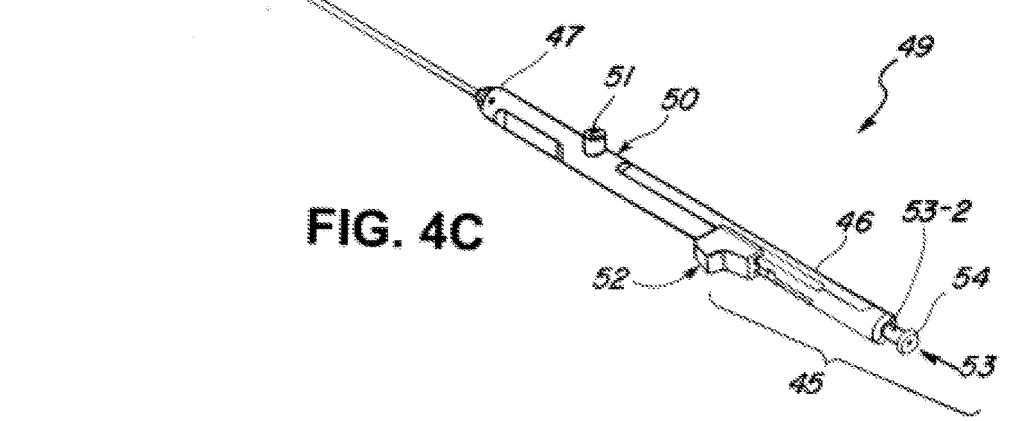
FIG. 4C shows an oblique view of the needle with the snare fully extended.

FIGS. 4A-4C illustrate a preferred embodiment of a dual insufflation and wound closure device, or simply needle apparatus, 49 which may be used in connection with the preferred guide discussed above. The needle apparatus 49 serves the dual purposes of insufflating an abdominal cavity as well as engaging and passing suture to close a wound. The needle apparatus 49 includes a puncture closure mechanism, or suture engaging mechanism, preferably comprising a deformable snare 57 movable between three functional positions as depicted in FIGS. 4A-4C. The suture snare 57 may be fully retracted within a needle shaft assembly, or simply needle shaft, 55 (FIG. 4A), partially extended (FIG. 4B) to a temporary fixed position, or fully extended (FIG. 4C). The snare 57 may comprise a single wire or, preferably, a plurality of interwoven strands to reduce strain and allow for a greater angle of flexure. The snare may also include in curvature in shape to reduce stain and prevent the snare from experiencing permanent deformation. In the preferred embodiment, the deformable snare 57 is composed of a shape memory alloy material such as Nitinol, but may also be made from other metallic or polymeric wire materials.

In the preferred embodiment, a rod assembly, or slide rod, 53 is coupled to the snare 57. The rod assembly 53 comprises a rod distal portion 53-1 connected to the snare 57 and disposed within the shaft assembly 55 and a rod proximal portion 53-2 protruding out from the housing proximal portion 46. In the preferred embodiment, the rod distal portion 53-1 is integral with the rod proximal portion 53-2, although the two rod portions 53-1, 53-2 may comprise separate pieces axially coupled to each other.

In the preferred embodiment, a dual actuator mechanism 45 disposed adjacent to a proximal end of the needle housing 50 controls the position and configuration of the snare 57. The dual actuator mechanism 45 preferably comprises a first actuator 53 configured to move the snare 57 between the fully exposed position and the fixed partially exposed position, and a second actuator 52 configured to move the snare 57 between the fixed partially exposed position and a fully retracted position. The needle housing 50 comprises a housing proximal portion 46 and a housing distal portion 47.

The first actuator 53 preferably comprises a slide rod, or extender rod, 53, axially protruding out from the housing proximal portion 46. A knob 54 may be coupled to the proximal end of the rod proximal portion 53-2 to facilitate use of the first actuator 53. In the preferred embodiment, the slide rod 53 is slidably disposed within the needle housing 50, and coupled to the snare 57 that travels through the needle housing 50 and needle shaft 55 to the distal tip of the needle 56. When the slide rod 53 is fully pushed into the needle housing 50 in a distal direction, the snare 57 is fully extended (as in FIG. 4C).

Since the deformable snare 57 is composed of a material having shape memory characteristics, the snare 57 is pre-configured to form a loop that is substantially perpendicular to the shaft axis A when fully exposed. In this fully exposed configuration as shown close-up in FIG. 11, the snare 57 forms an elongate loop having a distal loop tip 61 connected to a pair of distal loop sections 62, which are preferably linear, which are connected to arched majority loop sections 63. As the snare 57 is moved from the partially exposed position to the fully exposed position, the snare 57 forms a loop that not only increases in size, but also curves back towards the shaft 55 to form a perpendicular orientation with respect to the shaft axis "A." Thus, the snare 57 travels an arcuate path bent towards the shaft 55 as the snare 57 moves from the partially deployed to the fully deployed configuration.

When the slide rod 53 is proximally pulled toward an extended, protruding position as shown in FIG. 4B, the deformable loop decreases in size as the snare 57 is retracted into the needle distal tip 56. When pulled in the proximal direction, the slide rod 53 will continue to retract the snare 57 until the distal loop tip 61 contacts the exit ramp of the obturator. The first actuator 53 is partially spring loaded in a manner that only when the slide rod 53 nears the fully extended proximal position, the slide rod 53 engages the first spring mechanism 64 which biases the slide rod 53 distally to a rest position. This spring-biased rest position corresponds to the fixed partially exposed position of the snare 57, shown in FIGS. 4B and 9. It will be appreciated that the partially exposed position as shown in FIG. 4B is fixed in the sense that further retraction of the snare 57 beyond this point requires actuation of the second actuator, which in the preferred embodiment comprises proximal movement of the thumb slide 52 as discussed further below.

Figure 6A:
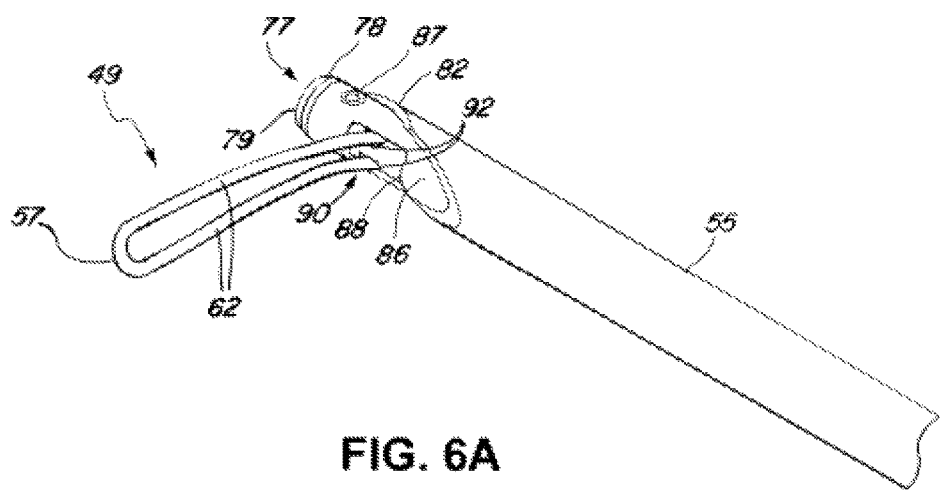
FIG. 6A is a detail view of the distal tip of the needle with the spring loaded safety obturator.

This partial spring loading of the slide rod 53 allows for the snare 57 to rest in the fixed partially exposed without actuation. In this fixed partially exposed configuration, the snare 57 protrudes sideways from the needle shaft 55 and forms a substantially planar loop where the two linear loop sections 62 are substantially parallel to each other as shown in FIG. 6A. This planar loop is off-axis with respect to the shaft axis "A." Thus, in either the partially exposed or fully exposed position, the deformable loop is slanted with respect to the axis "A" of the shaft assembly 55. Since the snare 57 is substantially planar in this fixed, partially exposed position, the loop snare 57 travels linearly as it is further retracted into a fully hidden, retracted position.

The second actuator 52, which comprises a lockout trigger or thumb slide in the preferred embodiment, controls movement of the snare 57 from the fixed partially exposed configuration to the fully retracted position, and locks the snare 57 in the fully retracted configuration. When the slide rod 53 is proximally extended to the spring biased rest position, a mating mechanism is provided between the slide rod 53 and the trigger 52 such that proximal actuation of the trigger 52 moves the slide rod 53 proximally which further retracts the snare 57. In the preferred embodiment, the mating mechanism comprises a notch 66 formed in the slide rod 53 which is configured to mate with an inwardly protruding fin 67 of the trigger 52.

When the slide rod 53 is in the spring-biased rest position, the notch 66 is aligned with the fin 67 such that proximal movement of the trigger 52 engages the slide rod 53 and pulls the slide rod 53 out to its most extended proximal position which fully retracts the snare 57. The lockout trigger 52 is then locked to the needle housing 50 by mating features between the two. In the preferred embodiment, a tongue 68 on the trigger 52 mates with a groove 69 formed in the sidewall of the housing 50. To unlock the trigger 52, the distal end 71 of the trigger 52 can be slightly lifted away from the needle housing 50 to release the tongue 68 from the groove 69. A second spring mechanism 73 biases the trigger 52 distally and moves the unlocked trigger 52 to its proximal most position, at which point the trigger 52 is released from the slide rod 53. When the trigger 52 is unlocked from the housing 50 disengaged by the user, the first and second spring mechanisms 64, 72 distally urge the first and second actuators 53, 52, respectively, thereby returning the extender to the rest position allowing for partial exposure of the wire snare 57 (as in FIG. 4B).

In the preferred embodiment shown in FIG. 6 C, the lockout trigger 52 is disposed on an outer surface 73 of the cylindrical housing sidewall 74 opposite to the exit of the snare and constrained by side tracks 75 and a top slot 76. Other features on the housing outer wall 74 may be employed to constrain the trigger 52. As the trigger 52 is pushed distally by the second spring mechanism 72, the trigger 52 rides along the ramped tracks 75 and through the top slot 76 formed in the housing sidewall 74 which separate the slide 52 from the rod 53 and facilitates disengagement thereof.

Figure 5A:
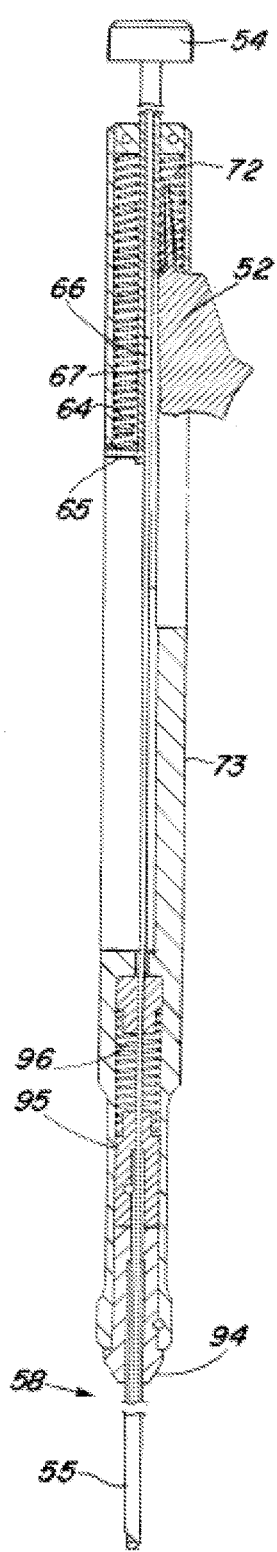
FIG. 5A is a cross-sectional view of the needle housing showing the internal components of the needle corresponding to the fully retracted snare position in FIG. 4A.

Referring back to FIG. 4A, the needle housing 50 may also have a quick connect mechanism, such as a luer connection 51 somewhere along its length. The luer connector 51 allows for an inert gas line to be connected to the needle apparatus 49. As the gas enters the needle apparatus 49, it flows distally through the hollow insufflation lumen, or insufflation channel, 41 of the needle shaft 55 and exits the needle apparatus 49 at the distal tip. This allows for insufflation of the abdominal cavity. FIG. 5A is a detailed view of the needle apparatus 49 showing a first preferred embodiment of a blunt obturator assembly 77 of particular use when the needle apparatus 49 is used as an insufflation device.

In FIG. 6A, the obturator assembly 77 comprises a first preferred blunt obturator tip 78 having a generally flat top 79 at a distal end. The needle shaft 55 has a sharp needle tip 82 at a distal end preferably comprising a needle peak 83 and a pair of blade edges 84 extending proximally and laterally therefrom, as shown in FIGS. 7A-7D. The needle tip 82 facilitates insertion of the needle shaft 55 through the tissue layers. In order to prevent damage to the underlying organs, the spring loaded blunt obturator tip 78 is slidably disposed within the needle shaft 55. The blunt obturator tip 78 is connected to an obturator shaft 86 by a dowel pin 87. A window cutout 88 in the obturator shaft 86 provides a location for the snare 57 to exit the needle apparatus 49. The blunt obturator tip 78 partially extends up the length of the obturator shaft 86. An exit section 90 adjacent to the window cutout 88 has two tracks, or exit slots, 92 to accommodate the passage of the snare 57. The preferably two distinct tracks 92 prevent the snare 57 from being pulled all the way up the needle shaft 55, or becoming twisted as it is retracted and extended from the shaft 55.

Figure 6B:
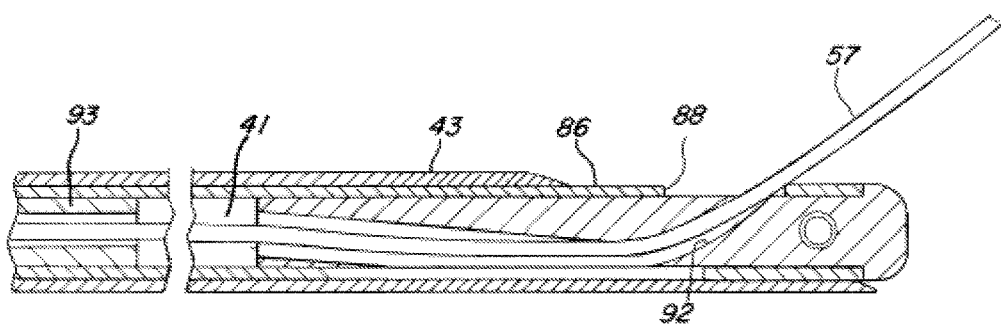
FIG. 6B is a cross-sectional view of the distal tip of the needle.

FIG. 6B shows a cross-sectional view of the distal tip of the needle instrument. One of the needle tracks 92 is shown to guide the wire snare 57 distally out the window cutout 88 in the obturator shaft 86. The needle tracks 92 also guide the snare 57 proximally into the push rod 93 that extends proximally.

In the preferred embodiment, the shaft assembly 55 comprises an inner snare push rod 93 disposed within the obturator shaft 86, which is disposed with an outer shaft 43 that forms the distal needle tip. The inner obturator shaft 86 defines the insufflation lumen 41.

Referring back to FIG. 5A, the internal workings of the needle apparatus 49 are shown in FIG. 6. The needle shaft 43 is connected to the distal end 58 of the needle housing 50 via a needle hub 94. The obturator shaft 86 which is slidably disposed within the needle shaft 55, connects to a obturator hub 95 that is proximal to the needle hub 94. The obturator hub 95 is slidably disposed within the needle housing 50 and spring loaded by a spring 96 that allows the obturator shaft 86 to translate as the obturator tip 78 is pressed against.

Figure 5B:
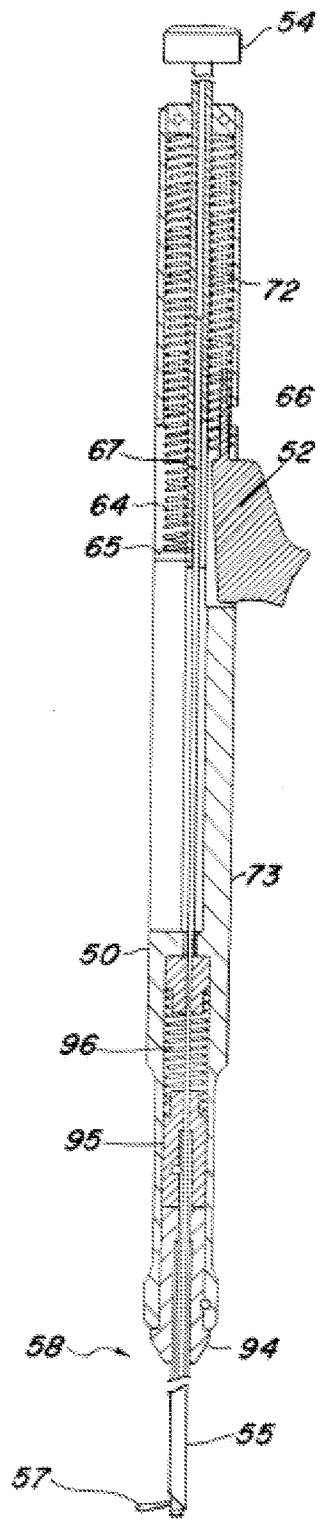
FIG. 5B is a cross-sectional view of the needle corresponding to the partially extended snare position shown in FIG. 4B.
Figure 5C:
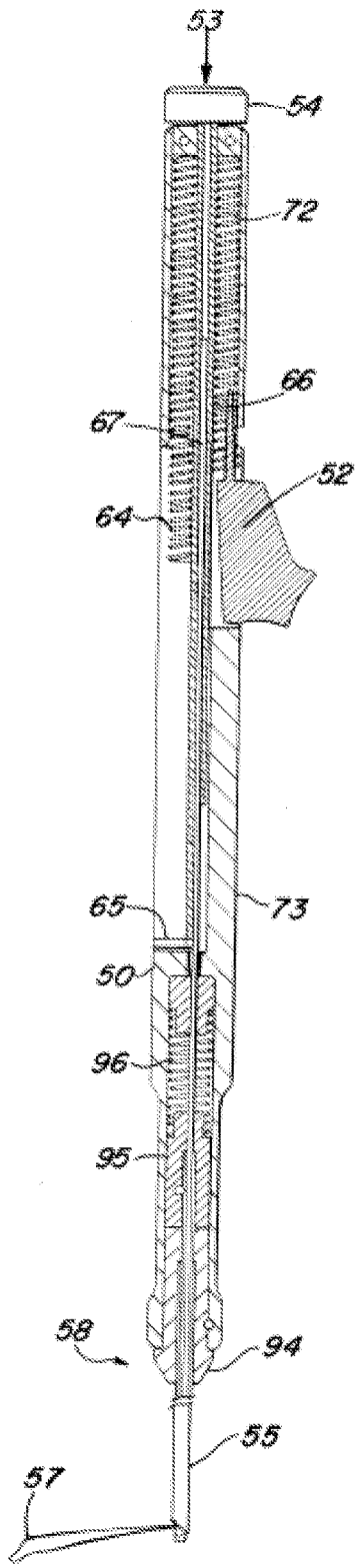
FIG. 5C is a cross-sectional view of the needle corresponding to the fully extended snare position shown in FIG. 4C.

The snare push rod 93 is slidably disposed within the needle housing 50 and the obturator shaft 86 and fixed to the slide rod 53. The snare 57 is fixed to the proximal end 59 of the slide rod 53 and travels through the slide rod 53, through the snare push rod 86, and ultimately out through the obturator tip 78 (as shown in FIG. 5). Since the snare 57 is flexible, it requires passage through rigid structures so that it can extend and retract at the needle tip.

At the proximal end of the slide rod 53 is a slide rod pin 65 that may serve multiple purposes. The pin 65 helps to maintain the rotational alignment of the slide rod 53 within needle housing. The pin 65 also engages the first spring mechanism, or the slide rod spring, 64 when the snare 57 approaches retraction back into the needle, partially spring loading the travel of the slide rod 53 distally back to the rest position.

As discussed above, the trigger 52 is also spring loaded by a second spring mechanism, or trigger spring, 72, causing the trigger 52 to be biased in the distal direction. As the trigger 52 is pulled proximally, it engages with the slide rod 53, and pulls it back against the force of the slide rod spring 64. The lockout trigger 52 can then be locked to the needle housing 50, locking out the snare 57 in the fully retracted position. Both the trigger spring 72 and slide rod spring 64 are constrained to the needle housing 50 by proximal plugs 98 that may be pinned to the needle housing 50.

Figure 7C:
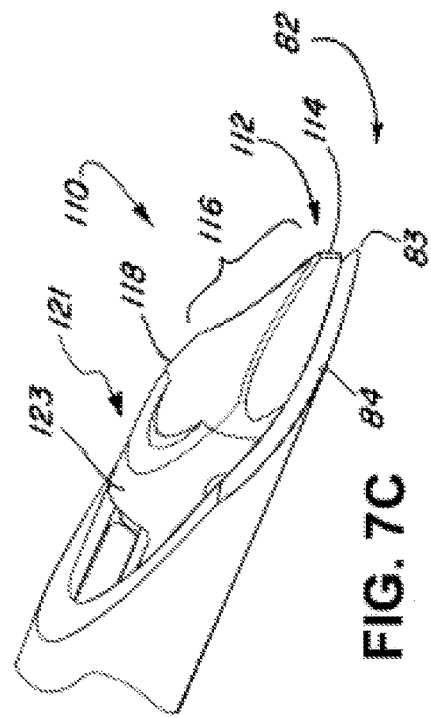
FIG. 7C is an oblique view of an alternative retractable obturator tip design.
Figure 7A:
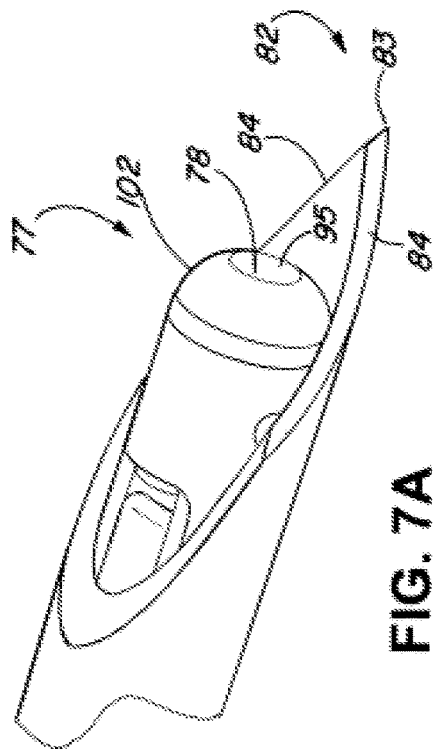
FIG. 7A is an oblique view of a standard retractable obturator tip design.
Figure 7D:
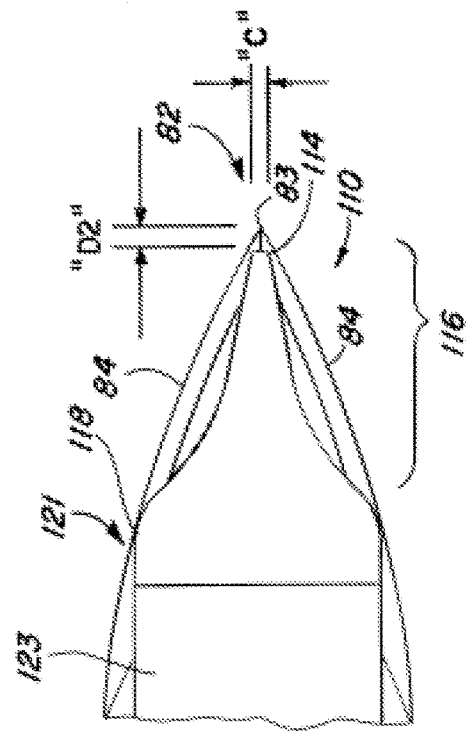
FIG. 7D demonstrates the relative distance from the tip of the needle to the tip of the alternative obturator.
Figure 7B:
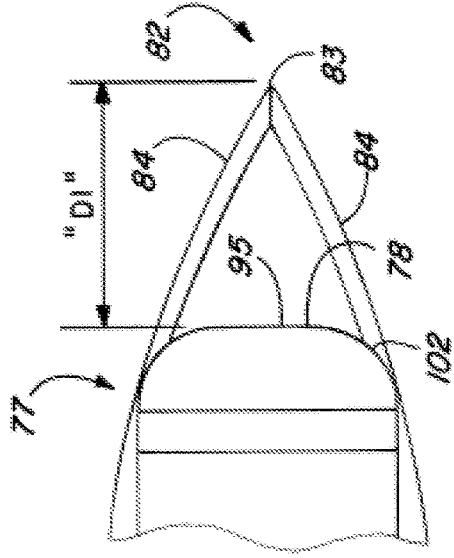
FIG. 7B demonstrates the relative distance from the tip of the needle to the tip of the obturator.

FIGS. 7A and 7B provide close-up view of the obturator assembly 77 with the flattop obturator tip 78. The flattop obturator tip 78 has a flat front 95 with rounded corners 102.

FIGS. 7C and 7D show a second preferred obturator assembly 110 having a unique ramped obturator tip 112. The ramped tip obturator tip 112 comprises an obturator peak 114 with a smaller cross sectional area "C", allowing for more exposure of the sharpened blade edges 84 of the outer needle shaft 55. In the preferred embodiment, the ramped surfaces 116 are positioned proximally to the blade edges 84 when the obturator peak 114 distally traverses the needle peak 83 up to 5 mm. The obturator peak 114 defines a surface area preferably less than 0.1 square mm. In the preferred embodiment, the surface area of the obturator peak 114 is 0.06 square mm or less. Moving proximally away from the distal obturator peak 91, the cross-sectional area of a tapered section 116 increases in area, until the area at the base 118 of the tapered section 116 is equivalent to the distal end 121 of the obturator tube 123. FIG. 7B shows the distance "D1" the flattop distal tip 85 needs to be from the needle peak 83 to expose the sharp needle edges 84. FIG. 7D shows this a shortened distance "D2" with the ramped obturator tip design 110 between the needle peak 83 and the obturator peak 114. This preferred ramp obturator tip 110 allows the spring loaded obturator mechanism to advance in a quicker manner through the tissue layer and thus provide enhanced safety by reducing the exposure time of the sharp needle peak 83. The preferred ramp obturator 110 may also facilitate the ease of insertion of the needle through the tissue layers.

Alternative ergonomic handle designs are proposed in FIGS. 8A-8C. In FIG. 8A a simplified alternative handle design is shown, compared to the primary embodiment disclosed above. A handle 130 is shown with two extension tabs 134 that can be supported in the hand by two fingers (such as the index and middle finger). The plunger 136 has a surface 138 that can be pressed by another finger (such as the thumb) in order to advance the plunger 136 and deploy the snare. The plunger 136 may be spring loaded with respect to the handle 130, so that the plunger 136 is biased in the direction that retracts the snare.

In FIG. 8B, an alternative preferred embodiment of a handle 140 comprises two finger slots 142 each configured to receive a finger, and a hole 144 formed on the plunger 146 for receiving a thumb. As the thumb slides distally, the plunger 148 also advances distally inside the handle 140, deploying the snare.

In FIG. 8C, a further preferred embodiment of a handle 150 comprises an inverted design with respect to the embodiment shown in FIG. 8B. Here, two fingers (such as the index and middle fingers) can be placed inside the finger slots 152 on the plunger 154, while another finger (such as the thumb) can be placed in the hole 156 of the handle 150. In this embodiment, the two fingers in the plunger 154 would be advanced distally to deploy the snare.

The following describes a preferred method of wound closure or suture passing using the first preferred embodiment of the wound closure system described above in connection with FIGS. 1-6. The guide plunger 21 is translated, preferably pressed down, to contract the feet 26, and causing the guide 10 to take a slender, continuous profile as shown in FIG. 1B. With the plunger pressed down and the guide taking a slender profile, the guide 10 is inserted through the tissue, particularly through a surgical wound or opening. The plunger 21 is released and the expanding feet 26 are placed against the peritoneal wall (FIG. 3).

Figure 9:
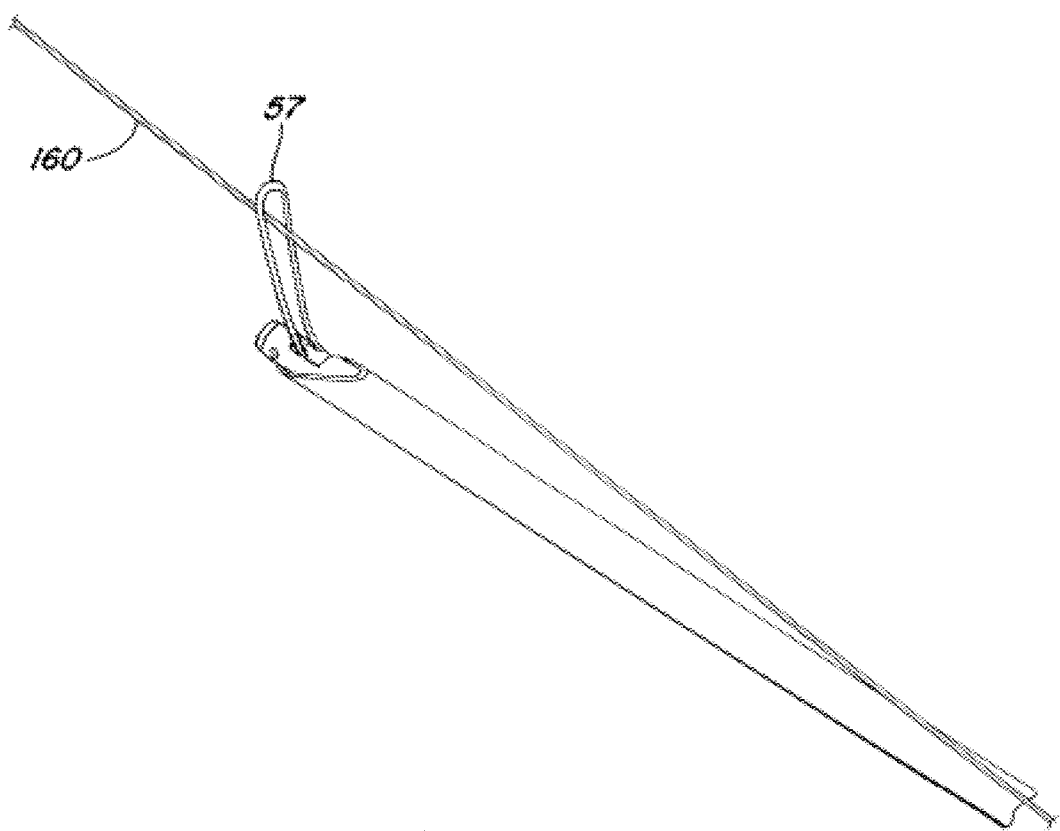
FIG. 9 shows the suture being loaded into the snare.

With the guide 10 inserted through the trocar wound and secured to the inner wall, attention is turned to the needle apparatus 49 which also functions as a suture engaging device. The lockout trigger 52 is released to partially extend the snare 57 (FIG. 4B). In FIG. 9, a section of suture 160 is placed into wire snare 57. As shown in FIGS. 4A and 5A, the lockout trigger 52 is actuated and the snare 57 is retracted to capture the section of suture 160 within the distal tip of the needle apparatus 49.

Figure 10:
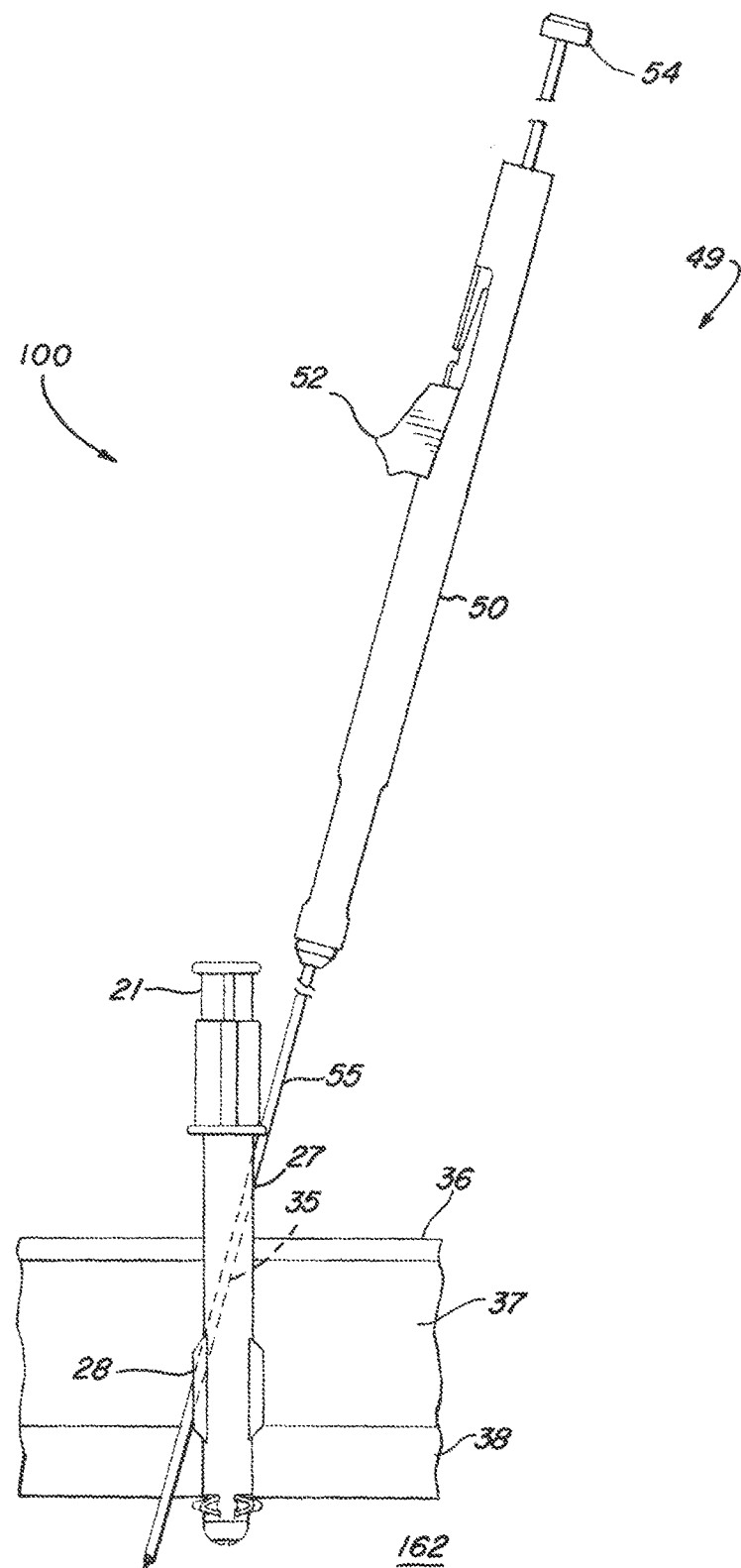
FIG. 10 shows the needle passing suture through the guide and tissue.

In FIG. 10, the needle apparatus 49 is then placed through one of the guide barrel needle entry slots 27, through the needle tunnels 35 in the plunger 21, out the needle exit slots 28, and through the tissue 36, 37, 38 into the abdominal cavity 162. The lockout trigger 52 is released (see FIGS. 4B and 5b), deploying the snare 57. The needle apparatus 49 can then be further advanced into the cavity 162 to release the section of suture 160. The lockout trigger 52 is again actuated to retract the snare 57, and the needle apparatus 49 is removed from the guide 10 and tissue layers 36, 37, 38. The needle apparatus 49 is then inserted into the opposing needle entry slots 27 of the guide 10 and through the tissue layers 36, 37, 38. The lockout trigger 52 is released to partially deploy the wire snare 57. The slide rod 53 is fully translated into the needle housing 50 to fully deploy the snare 57. The needle 49 can then be rotated or manipulated to place the snare 57 underneath the free end of the suture 160.

Figure 11:
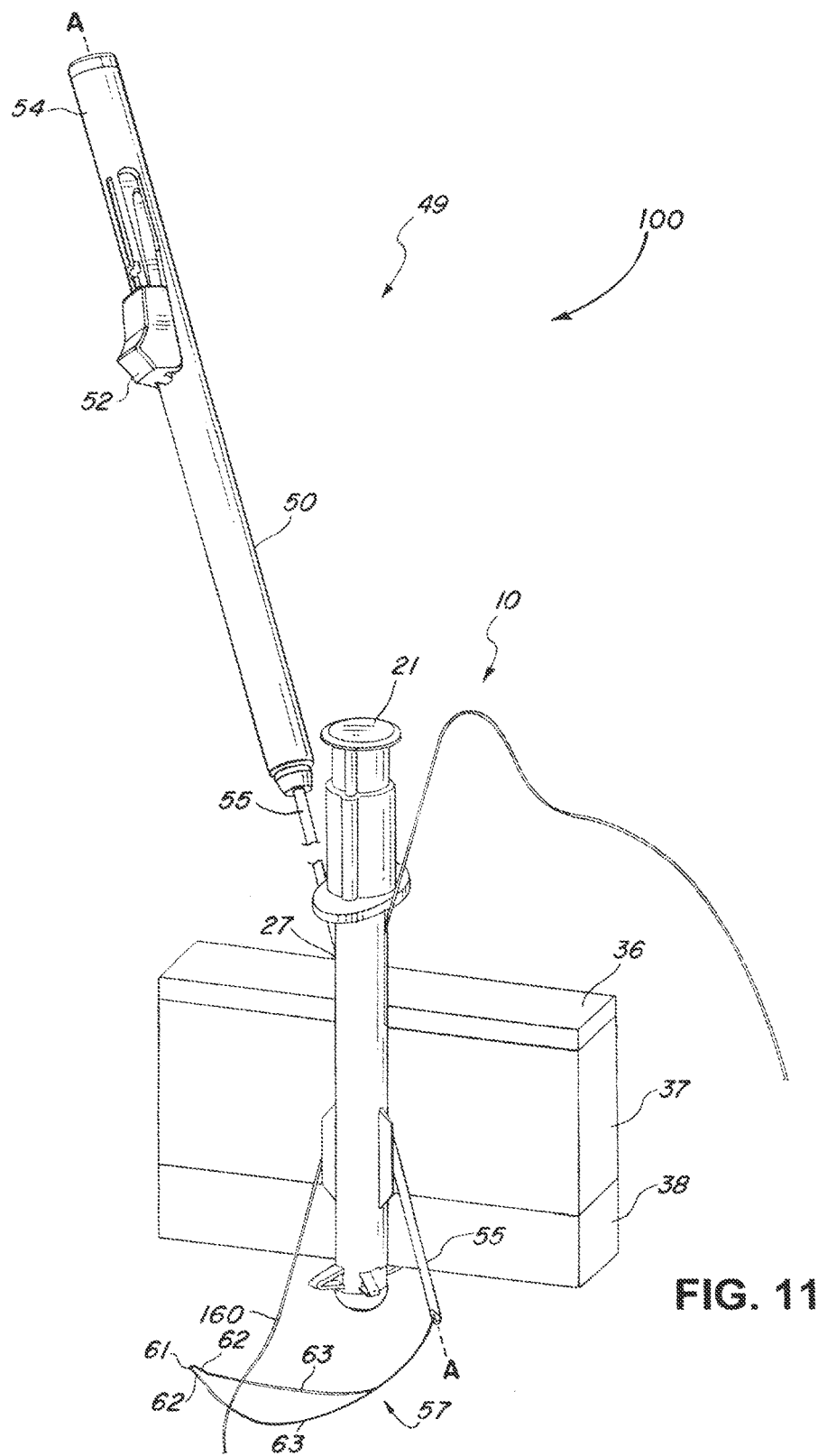
FIG. 11 shows the needle being used to retrieve the free end of the suture.

In FIG. 11, the needle apparatus 49 is then slightly pulled proximally to encircle the suture 160 inside the snare 57. The slide rod 53 is pulled back proximally to the spring-biased rest position, and the lockout trigger 52 is actuated to capture the suture 160 in the tip of the needle apparatus 49. The needle apparatus 49 is then pulled out of the body and guide 10. One last time the lockout trigger 52 is released to partially extend the snare 57. The suture 160 is then removed from the snare 57. The guide is then removed to freely expose the suture ends. A knot is tied between the two free ends of the suture 160 that is used to close the wound site.

Figure 12:
FIG. 12 illustrates a preferred method for insufflating a body cavity and engaging a suture to close a wound using a single device.

FIG. 12 illustrates a preferred method 200 for insufflating a body cavity and engaging a suture to close a wound using a single device. The method 200 comprises the step 210 of insufflating the body cavity with a shaft defining an insufflation channel along an axis between a shaft distal end and a shaft proximal end. Step 220 comprises securing a suture with a snare disposed adjacent to the shaft distal end. In step 230, the shaft with the secured suture is inserted into the body cavity at a desired first location. A guide may be used in step 230 to direct the device to the desired first location. In step 240, the suture is released by moving, or actuating, the snare to an exposed position, which may be a partially exposed or fully exposed position. Step 250 comprises removing the shaft from the first location.

In step 260, the shaft is inserted into the body cavity at a desired second location spaced apart from the first location. The guide may be used in step 260 to direct the shaft to the second location. Step 270 comprises capturing the suture with the snare. In step 270, the snare may be actuated to a fully exposed position to enlarge the loop and orient the loop substantially perpendicular to the axis of the shaft. Step 280 comprises securing the suture to the shaft by retracting the snare. Step 290 comprises removing the shaft from the second location with the secured suture to complete a stitch loop.

Figure 13:
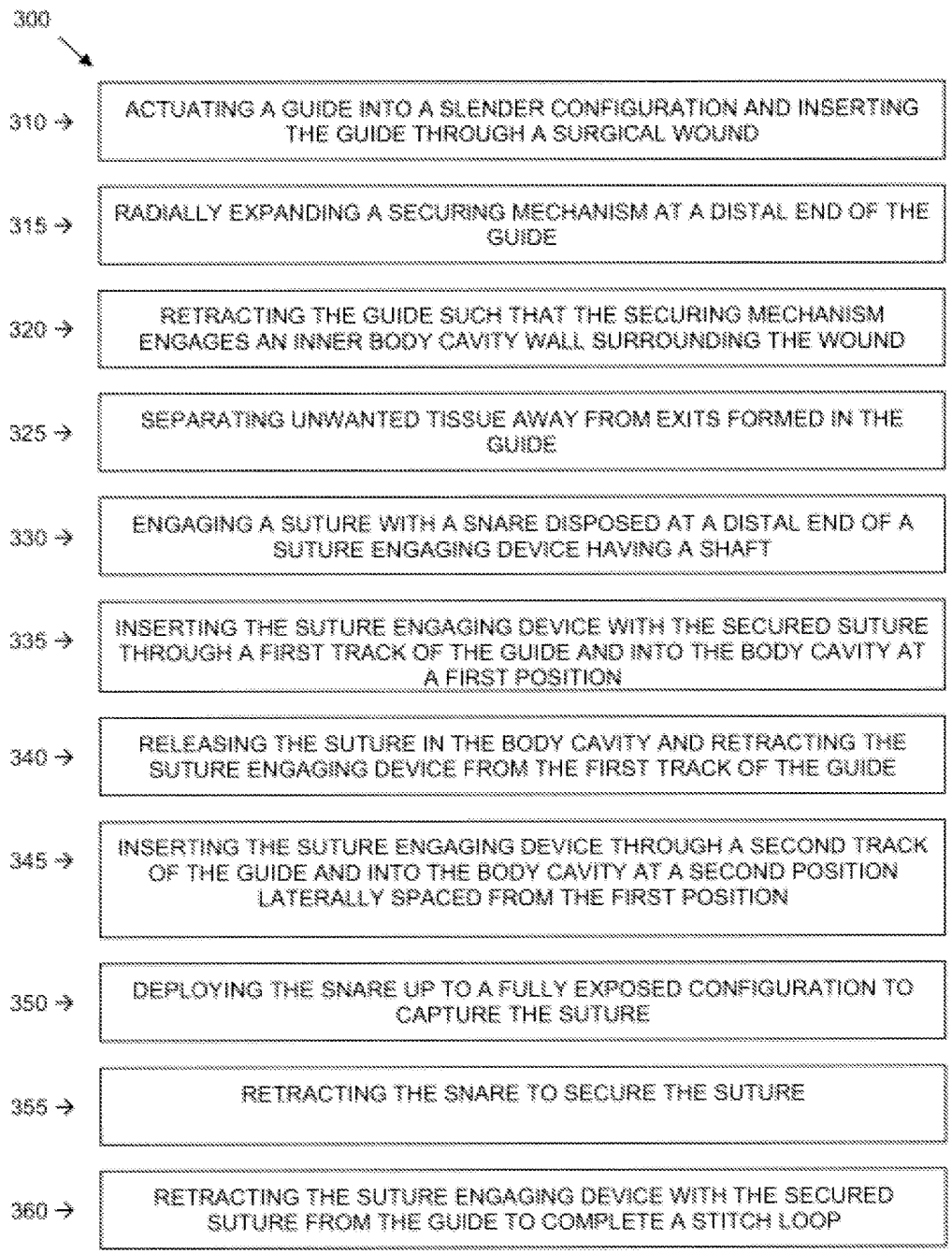
FIG. 13 illustrates a preferred method for closing a surgical wound using a system comprising preferred embodiments of a guide and a suture engaging device disclosed above.

FIG. 13 illustrates a preferred method 300 for closing a surgical wound using a system comprising preferred embodiments of a guide and a suture engaging device disclosed above. It will be appreciated that this method 300 enables an operator to deploy and capture suture using simply a guide and a suture engaging device without the need for a grasper. The method 300 comprises the step 310 of actuating a guide into a slender configuration and inserting the guide through surgical wound. Step 315 comprises radially expanding a securing mechanism, which may comprise feet or living hinges, at a distal end of the guide. Step 320 comprises retracting the guide such that the securing mechanism engages an inner body cavity wall surrounding the wound. In step 325, unwanted tissue is separated away from exits formed in the guide in order to prevent said tissue from being sutured. Step 325 may be accomplished with axial wings formed on an outer surface of the guide adjacent to the exit slots.

Step 330 comprises engaging a suture with a snare disposed at a distal end of a suture engaging device having a shaft. In step 330, the snare is actuated to a fully retracted position to capture and lock the suture. Step 335 comprises inserting the suture engaging device with the secured suture through a first track of the guide and into the body cavity at a first position. Step 340 comprises releasing the suture in the body cavity and retracting the suture engaging device from the first track of the guide. Step 345 comprises inserting the suture engaging device through a second track of the guide and into the body cavity at a second position laterally spaced from the first position. In Step 350, the snare may be deployed up to a fully exposed configuration to capture the suture. In the fully exposed configuration, the loop is substantially perpendicular to the axis of the shaft of the suture engaging device. Step 355 comprises retracting the snare to secure the suture. Step 360 retracting the suture engaging device with the secured suture from the guide to complete a stitch loop.

FIG. 14 illustrates a second preferred embodiment of a needle apparatus 400 comprising a single actuator 452 as opposed to dual actuators included in the first preferred needle apparatus discussed above. In this second preferred needle apparatus 400, the actuator 452 comprises a lockout trigger 452 coupled to a rod assembly 448 that is coupled to a snare 457. Whereas in the first preferred needle apparatus, the lockout trigger is capable of moving the snare between a retracted position to a partially exposed position, the lockout trigger 452 in the second preferred needle apparatus 400 is capable of moving the snare 457 between a retracted position, where the trigger 452 is moved to the most proximal position as shown in FIG. 15, and a fully exposed position, where the trigger is moved to the most distal position as shown in FIG. 14.

The lockout trigger 452 rides along a top slot 476 and a pair of side tracks 475 formed in the housing 450. Since the lockout trigger 452 needs to translate a greater distance with respect to the housing, particularly in the proximal direction, the slot 476 and tracks 475 are formed with greater lengths than those of the first preferred needle apparatus 49.

Figure 6C:
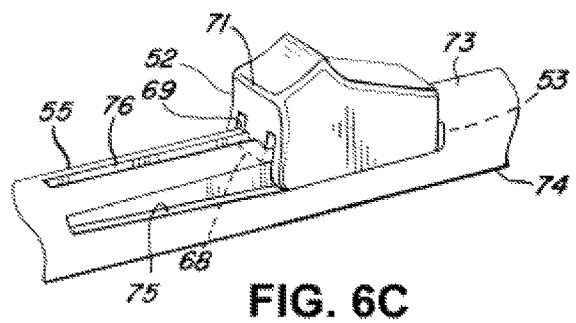
FIG. 6C is a close-up perspective of the housing of the needle apparatus showing a preferred lockout trigger.

Accordingly, the slide rod 53 of the first preferred needle apparatus 49 shown in FIGS. 6A-6C, has been omitted in the second preferred needle apparatus 400 and replaced by the single lockout trigger 452. Furthermore, the second preferred needle apparatus comprises a 402 which may be formed integrally with or separately from the housing 450. The handle 402 defines a finger slot 403. Except for structural differences discussed above with respect to FIGS. 14-15, all other structures in the second preferred needle apparatus 400 as well as the principles of operation are substantially similar to those in the first preferred needle apparatus 49.

Many alterations and modifications may be made by those having ordinary skill in the art without departing from the spirit and scope of the invention. Therefore, it must be understood that the illustrated embodiments have been set forth only for the purposes of examples and that they should not be taken as limiting the invention as defined by the following claims. For example, notwithstanding the fact that the elements of a claim are set forth below in a certain combination, it must be expressly understood that the invention includes other combinations of fewer, more or different ones of the disclosed elements.

The words used in this specification to describe the invention and its various embodiments are to be understood not only in the sense of their commonly defined meanings, but to include by special definition in this specification the generic structure, material or acts of which they represent a single species.

The definitions of the words or elements of the following claims are, therefore, defined in this specification to not only include the combination of elements which are literally set forth. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a sub combination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements. The claims are thus to be understood to include what is specifically illustrated and described above, what is conceptually equivalent, what can be obviously substituted and also what incorporates the essential idea of the invention.

What is claimed is:

1. A method of suturing a trocar port site wound comprising:
   a) pressing a spring biased plunger of a guide to move radially expanding feet from a biased extended position to a slender configuration, the feet being orthogonal to exits of first and second tracks in the guide;
   b) inserting the guide by linear translation in the slender configuration into a wound site created by a trocar, until the retracted feet of the guide are through the surgical wound;
   c) releasing the spring biased plunger of the guide to allow the biased feet to extend radially at opposite locations orthogonal to the exits of the first and second tracks;
   d) retracting the guide to position the guide such that the expanded feet are placed against a peritoneal tissue;
   e) grasping a suture with a wound closure device;
   f) passing the suture with said wound closure device through the first track in the guide and into the body cavity at a first position;
   g) releasing the suture at the first position;
   h) retracting the wound closure device from the guide, leaving the suture in place;
   i) inserting the wound closure device in the second track defined within the guide and into the body cavity at a second position laterally spaced from the first position;
   j) retrieving the suture from the first position with the wound closure device, and retracting the wound closure device with the suture from the guide;
   k) pressing the spring biased plunger of the guide to move the radially expanding feet from the biased extended position to the slender configuration;
   l) removing the guide in the slender configuration from the wound site to freely expose suture ends; and
   m) tying a knot between the suture ends of the suture to provide closure of the wound.

2. The method of claim 1, wherein the inserting said wound closure device in said second track comprises exiting the second track at the second position located 180 degrees from the first position.

3. The method of claim 2, wherein the first track is oblique to an axis of the guide.

4. The method of claim 3, wherein the second track is both oblique to the axis of the guide and diagonal to the first track.

5. The method of claim 1, wherein:
   the first track initiates at a first entry slot disposed in a barrel proximal portion located at a first side portion of the guide; and
   the second track initiates at a second entry slot disposed in the barrel proximal portion located at a second side portion of the guide opposite to the first side portion of the guide.

6. A method of suturing a trocar port site wound comprising:
   a) pressing a spring biased plunger of a guide to move a first living hinge and a second living hinge from a biased extended configuration to a slender configuration, the living hinges being orthogonal to exits of first and second tracks in the guide;
   b) inserting the guide by linear translation in the slender configuration into a wound site created by a trocar, until the living hinges are through the surgical wound;
   c) releasing the spring biased plunger of the guide to allow the first living hinge and the second living hinge to extend radially expanding feet at locations opposite to each other and orthogonal to the exits of the first and second tracks;
   d) retracting the guide to position the guide such that the living hinges are placed against a peritoneal tissue;
   e) grasping a suture with a wound closure device;
   f) passing the suture with the wound closure device through the first track in the guide by entering a first entry slot that initiates in a first side portion of the guide and into the body cavity at a first position;
   g) releasing the suture at the first position;
   h) retracting the wound closure device from the guide, leaving the suture in place;
   i) inserting the wound closure device in the second track by entering a second entry slot that initiates in a second side portion of the guide opposite to the first side portion of the guide, and into the body cavity at a second position spaced 180 degrees from the first position;
   j) retrieving the suture in the first position with the wound closure device, and retracting the wound closure device with the suture from the guide;
   k) pressing the spring biased plunger of the guide to move the radially expanding feet from the biased extended position to the slender configuration;
   l) removing the guide in the slender configuration from the wound site to freely expose suture ends; and
   m) tying a knot between the suture ends of the suture to provide closure of the wound.

7. The method of claim 6, wherein the first track is oblique to an axis of the guide.

8. The method of claim 7, wherein the second track is both oblique to the axis of the guide and diagonal to the first track.

9. A method of suturing a trocar port site wound comprising:
   a) allowing radially expanding feet of a guide with a spring biased plunger to extend radially at opposite locations at a distal end of the guide after the guide is inserted into a wound site, the feet being orthogonal to opposing first and second exits of the guide;

b) retracting the guide to position the guide such that the expanded feet are placed against a peritoneal tissue;

c) grasping a first end of a suture with a wound closure device;

d) passing the suture with said wound closure device through the guide by entering a first entry slot that initiates in a first side portion of the guide and exiting the first exit to pass through tissue at a first position, and into the body cavity;

e) releasing the first end of a suture in the body cavity;

f) retracting the wound closure device from the guide, leaving the suture through the tissue and in the body cavity;

g) inserting the wound closure device through the guide by entering a second entry slot that initiates in a second side portion of the guide opposite to the first side portion of the guide and exiting the second exit to pass through tissue at a second position laterally spaced from the first position and into the body cavity;

h) retrieving the first end of the suture with the wound closure device and retracting the wound closure device with the suture from the guide to create a stitch.

10. The method of claim 9, wherein said inserting said wound closure device comprises exiting the second position at an opposite side of the first position.

11. The method of claim 9, further comprising:

i) freely exposing suture ends; and j) tying a knot between the suture ends of the suture to provide closure of the wound.

12. The method of claim 9, wherein:

entering the first entry slot formed in the first side portion of the guide comprises entering a first side of a barrel proximal portion located at the first side portion of the guide; and entering the second entry slot in the second side portion of the guide comprise entering a second side of the barrel proximal portion located opposite to the first side of the barrel proximal portion.

* * * * *